US012742198B2

(12) United States Patent
Gao et al.

(10) Patent No.: US 12,742,198 B2
(45) Date of Patent: Sep. 22, 2026

(54) BIOCHIP AND MANUFACTURING METHOD THEREFOR

(71) Applicant: GeneMind Biosciences Company Limited, Shenzhen City (CN)

(72) Inventors: Jinhong Gao, Shenzhen City (CN); Zhi Zhao, Shenzhen City (CN); Luyang Zhao, Shenzhen City (CN); Qi Wang, Shenzhen City (CN); Fang Chen, Shenzhen City (CN)

(73) Assignee: GENEMIND BIOSCIENCES COMPANY LIMITED, Shenzhen City (CN)

( * ) Notice: Subject to any disclaimer, the term of this patent is extended or adjusted under 35 U.S.C. 154(b) by 1212 days.

(21) Appl. No.: 17/227,211

(22) Filed: Apr. 9, 2021

(65) Prior Publication Data

US 2021/0301331 A1 Sep. 30, 2021

Related U.S. Application Data

(63) Continuation of application No. PCT/CN2019/101068, filed on Aug. 16, 2019.

(30) Foreign Application Priority Data

Oct. 12, 2018 (CN) ......................... 201811191571.2
Oct. 12, 2018 (CN) ......................... 201811191589.2
Oct. 12, 2018 (CN) ......................... 201811191611.3

(51) Int. Cl.
*C12Q 1/6837* (2018.01)

(52) U.S. Cl.
CPC ................................. *C12Q 1/6837* (2013.01)

(58) Field of Classification Search
None
See application file for complete search history.

(56) References Cited

U.S. PATENT DOCUMENTS 9,670,445 B1 6/2017 Kuo et al.
10,837,879 B2 11/2020 Burns et al.
2003/0109062 A1* 6/2003 Inomata ........... G01N 33/54353 427/2.11
2009/0069232 A1* 3/2009 Callewaert ............ C12P 21/005 435/254.2
2012/0094354 A1* 4/2012 Lee ....................... G01N 33/02 422/500
2018/0127802 A1* 5/2018 Kendrick ............... C07K 16/40

FOREIGN PATENT DOCUMENTS

CN 1598587 A 3/2005
CN 1721429 A 1/2006
CN 101745495 A 6/2010
CN 101893634 A 11/2010
CN 102286371 A 12/2011
CN 102505041 A 6/2012
CN 103805718 A 5/2014
CN 104926923 A 9/2015
CN 106565824 A 4/2017
CN 107807239 A 3/2018
CN 109609333 A 4/2019
CN 109610006 A 4/2019
CN 109610007 A 4/2019
EP 1726661 A1 11/2006
EP 2607369 A1 6/2013
WO 9515970 A1 6/1995
WO 00/34456 A1 6/2000
WO 2006007207 A2 1/2006
WO 2006007207 A3 1/2006

(Continued)

OTHER PUBLICATIONS

"Microarray Overview" Genome Resource Facility, London School of Hygiene & Tropical Medicine, URL=http://grf.lshtm.ac.uk/microarrayoverview.htm, Accessed: Oct. 18, 2013, 7 pages.
Jonkheijm et al., "Chemical Strategies for Generating Protein Biochips," *Angew. Chem. Int. Ed. 47*:9618-9647, 2008.
Kane et al., "Kosmotropes Form the Basis of Protein-Resistant Surfaces," *Langmuir 19*:2388-2391, 2003.
Lai et al., "Enhancing the Fluorescence Intensity of DNA Microarrays by Using Cationic Surfactants," *Langmuir 27*:5659-5664, 2011.
Peng et al., "Recent developments in the fabrication of DNA microarrays," pp. 599-603, 2003. (with English translation; 7 pages).
Rossi et al., "Genome-wide determinants of sequence-specific DNA binding of general regulatory factors," *Genome Research 28*:497-508, 2018.

(Continued)

*Primary Examiner* — Christopher M Gross
(74) *Attorney, Agent, or Firm* — Seed Intellectual Property Law Group LLP

(57) ABSTRACT

A chip and a manufacturing method for the chip, comprising a weak passivation treatment following a fixing treatment. The weak passivation treatment comprises putting a weak passivation reaction solution containing a catalyst into contact with a chip for the fixing treatment, so as to promote a DNA or protein to bond with a substrate surface, thus allowing the DNA or protein to be fully fixed on the substrate surface. Moreover, on such basis, a small molecule or protein is added for manufacturing the chip. The utilization of the manufacturing method, with the step of weak passivation treatment added after the fixing treatment, allows the DNA or protein to be fully fixed on the substrate surface, not only increases the quality and efficiency of the fixing of the DNA or protein, but also reduces nucleotide and protein non-specific adsorption, thus allowing the volume of the DNA or protein being fixed to be highly controllable and to have good repeatability; moreover, when the chip is utilized for sequencing, the interference of a non-specific signal is reduced, thus laying the foundation for manufacturing a high-quality available DNA or protein chip.

6 Claims, 2 Drawing Sheets

(56) References Cited

FOREIGN PATENT DOCUMENTS

WO 2006/050617 A1 5/2006

OTHER PUBLICATIONS

Sun et al., "Characterization of Bovine Serum Albumin Blocking Efficiency on Epoxy-Functionalized Substrates for Microarray Applications," *Journal of Laboratory Automation and Screening*:1-7, 2005.

Wang et al., "Protein Resistant Materials and Their Applications in Biomedical Field," Polymer Bulletin, 2016. (with English translation; 30 pages).

Zhang et al., "Surface Inactivation Technology in PCR Bio-microfluidical Chip," *Analysis and Testing Technology and Instruments 11*(4):261-268, 2005. (with English translation; 18 pages).

* cited by examiner

BIOCHIP AND MANUFACTURING METHOD THEREFOR

This application claims the benefit of priority from Chinese Patent Application No. 201811191589.2, 201811191571.2 and 201811191611.3 all filed on Oct. 12, 2018, and from PCT Application No. PCT/CN2019/101068 filed on Aug. 16, 2019, the entire of which applications are hereby incorporated by reference in this application.

TECHNICAL FIELD

The present application relates to the field of biochip, and more particularly, to a biochip and a method for preparing the same.

BACKGROUND

DNA is an important genetic material of most organisms including humans. It contains a lot of important information, and provides key information for physiological and pathological detections. Efficient and accurate detection of DNA, particularly quantitative identification of the base variation in DNA sequence, has great scientific research significance and great clinical application value. Compared with other assays such as electrophoresis, PCR or test paper assay and the like, chip-based DNA assay features high throughput, good accuracy, convenience, automation, and other advantages. DNA chip is an important platform for chip-based DNA assay and is the basis for the detection reaction. For preparing a DNA chip, DNA should be robustly and efficiently immobilized on a substrate such as a glass, silicon or polymer substrate; moreover, the DNA immobilization method requires good reproducibility, stably and effectively producing DNA chips with consistency.

DNA chips with unreliable DNA immobilization are prone to the following defects: 1) a lower detection rate; 2) higher rates of false positive or false negative; 3) incorrect sequence information; and 4) poor reproducibility. In summary, the above defects may pose problems such as low cost efficiency and poor quality. Therefore, an efficient and convenient DNA immobilizing technique may improve the quality and reproducibility of the preparation method, and has great significance for improving the applicability and reducing the cost of the DNA chip.

Applicable DNA chips have to meet the following requirements: 1) immobilized DNA uniformly distributed on the substrate; 2) prepared chips having low nonspecific adsorption signals; 3) custom modified DNA species, i.e., various modified DNA chains; and 4) DNA chip preparing process having good reproducibility.

In the current DNA chip preparation method, common ways to immobilize DNA to a substrate includes: 1) covalent bonding; 2) physical adsorption; 3) specific linkage pairs, such as biotin/streptavidin pair. Among these, covalent bonding has the remarkable advantages such as high binding strength, and is widely used. However, as an active chemical reaction, covalent bonding has many problems in terms of controllability, reaction rate, and reproducibility. While using a DNA chip, the objects of detection include macromolecules and micromolecules.

Nonspecific adsorption may occur during the detection process of any molecule. Serious non-specific adsorption on the substrate of the chip may significantly affect the detection result. In many cases, preparing DNA chips of high applicability has to satisfy more stringent demands. In many scenarios, such as: 1) protein or nucleic acid assays, or 2) complex enzyme catalysis systems in sequencing, non-specific adsorption of proteins can have the following defects on the performance of DNA chips: 1) slight protein adsorption may bring non-specific signals, reducing the signal intensity and giving a low signal-to-noise ratio; and 2) serious protein adsorption may even completely block specifically modified DNA chains and disable the detection. More seriously, many adsorbed proteins carry various chemical groups and bring serious interference to the detection of certain chemical species. For example, glycans on glycoproteins interfere with the detection of polysaccharides, and sulfydryl groups on the proteins may bind to small molecules having sulfydryls in the assay system, bringing nonspecific signals, and nonspecific adsorption of nucleotide may pose problems such as inaccuracy.

In the DNA sequencing process, specific single-molecule signals and nonspecific adsorption signals are recognized and collected by an instrument, and the non-specific adsorption signals can seriously interfere the recognition of specific signals, so that great obstacle is formed to the later signal processing of the instrument.

Therefore, a well-designed chip preparation method has great value for improving the quality of DNA chips, as well as a chip with nonspecific adsorption resistance for the field of molecular detection.

SUMMARY

The present application is intended to provide an improved DNA or protein chip and a method for preparing the same, a method for immobilizing a DNA or protein, and use thereof. The chip produced by the preparation method of the present application has good reproducibility, controllability on amount of immobilized DNA or protein, and low adsorption capacity for protein or nucleotide.

The following technical solutions are disclosed herein:

According to one aspect of the present application, a method for preparing a DNA or protein chip is disclosed, comprising: performing weak passivation after immobilization, comprising contacting a weak passivation reaction solution with the chip after immobilization to promote the binding of a DNA or protein to a chip substrate surface, such that the DNA or protein is adequately immobilized on the substrate surface, wherein the weak passivation reaction solution contains a catalyst that promotes the binding of the DNA or protein to the substrate surface, thereby adequately immobilizing the DNA or protein on the substrate surface.

It should be noted that the present application includes a weak passivation procedure which is unexpectedly added in the preparation of the DNA or protein chip. In the weak passivation procedure, a catalyst is added to promote the binding of the DNA or protein to the substrate surface, such that the DNA or protein is more adequately immobilized on the substrate surface. It will be appreciated that the catalyst of the present application, which promotes the binding of DNA or protein to the substrate surface, is not specifically defined herein, and any compound or composition having such a function may be suitable for the present application. In the present application, the solution for weak passivation, i.e., the weak passivation reaction solution, may be a buffer suitable for a corresponding catalyst, as long as it has no adverse effect on the DNA, protein or substrate and promotes the binding of the DNA or protein. The amount of the catalyst in the weak passivation reaction solution, the temperature, time and pH of the reaction, and the other parameters may be adjusted according to the catalyst used, and are not specifically defined herein.

In addition, as the present application includes the added weak passivation procedure, for other procedures, such as immobilization, passivation, and subsequent washing, reference may be made to the prior art for preparing DNA or protein chips, and the substrate may be any of the conventional substrates, which are not defined herein.

It should be noted that, in one embodiment of the present application, the DNA or protein is specifically bound to the substrate surface through a covalent bond. Although existing covalent bonding reactions generally have the difficulties in control, the preparation method of the present application generates a more sufficient covalent bonding through the weak passivation and the addition of catalyst in the weak passivation procedure. The quantity of covalent bonds is closely related to the amount of DNA or protein added initially, such that the amount of DNA or protein immobilized is highly controllable, demonstrating good reproducibility. It will be appreciated that binding of the DNA or protein to the substrate surface may be covalent or non-covalent.

The above-mentioned catalyst is a surfactant selected from at least one of cetyltrimethylammonium bromide, dioctadecylammonium bromide, cetyltrimethylammonium chloride, dodecyltrimethylammonium bromide and tetraoctylammonium bromide.

It should be noted that in one embodiment of the present invention, the catalyst of the present application is preferably a cationic surfactant, which promotes the formation of a covalent bond between an amino group of DNA or protein and a modified group on the substrate surface. It will be appreciated that the catalyst is not limited to cationic surfactants, and other catalysts may be used for other types of covalent bonds. In one embodiment of the present application, the surfactant is specifically cetyltrimethylammonium bromide (CTAB). It will be appreciated that surfactants of similar function other than CTAB (such as dioctadecylammonium bromide, cetyltrimethylammonium chloride, dodecyltrimethylammonium bromide, and tetraoctylammonium bromide) that may promote the reaction between the amino group and modified group on the substrate surface are also applicable to the present application.

The concentration of the surfactant in the weak passivation reaction solution is 1-25 mmol/L. In one embodiment of the present application, the concentration of the surfactant in the weak passivation reaction solution is 10 mmol/L.

In one embodiment of the present application, the condition of weak passivation is 2-5 h at 35-40° C.

In one embodiment of the present application, the DNA in the above-mentioned preparation method of DNA chip carries an amino modification, and the substrate surface has a chemical modification. The chemical modification comprises active group selected at least one from epoxy group, formyl, carboxyl, N-hydroxysuccinimide and diaminobenzanilide. The catalyst promotes the reaction between the amino group of the DNA or protein and the active group on the substrate surface, such that the DNA or protein is adequately immobilized on the substrate surface.

It will be appreciated that as the protein is capable of reacting with the active group on the substrate surface to bind to the substrate surface, a protein may also have a modified group to facilitate binding to the substrate surface.

It should be noted that the amino modification is intended to form a chemical bond between the amino group and the modified group on the substrate surface. As such, based on purposes of DNA immobilization, amino modification may be performed on different nucleotides of DNA. The nucleotides can be positioned at the ends of the DNA, or any other positions. For example, the amino modification can be performed at 5', 3' or both ends of DNA, and the number of amino groups is not limited to one. It will be appreciated that a modified group containing an amino group capable of reacting with the group on the substrate is also applicable.

In one embodiment of the present application, the 3' end or 5' end of the DNA further comprises an optically detectable label. The optically detectable label may be a fluorophore, such as Cy3 or Cy5.

It should be noted that, since the fluorophore is intended to label the DNA for localization, any kind of fluorescence that does not affect DNA immobilization and can be used for DNA localization is applicable to the present application.

The immobilization of the present application comprises contacting an immobilization reaction solution containing the DNA with the substrate surface to immobilize the DNA. In one embodiment of the present application, the immobilization reaction solution is 0.25 mol/L $Na_2CO_3/NaHCO_3$ containing 0.6 mM CTAB, pH 9.78, wherein the concentration of DNA is generally 0.01-0.4 nmol/L, the temperature of immobilization is about 37° C., and the time for immobilization is about 30 min. The above conditions are for reference only, and are not specifically defined herein. The "$Na_2CO_3/NaHCO_3$" is composed of $Na_2CO_3$ and $NaHCO_3$, and the ratio of the two can be found in conventional method for DNA chip immobilization and is not specifically defined herein.

In one embodiment of the present application, the immobilization reaction solution contains the same catalyst as that in the weak passivation reaction solution. The concentration of the catalyst in the immobilization reaction solution is 0.01-0.10 nmol/L, specifically 0.05 nmol/L.

The preparation method of the present application further comprises passivation, comprising contacting a passivation reaction solution with the weakly passivated substrate surface. In one embodiment of the present application, the passivation reaction solution is 1 mol/L $K_2HPO_4/KH_2PO_4$, pH 9.0, wherein $K_2HPO_4/KH_2PO_4$ refers to a passivation reaction solution composed of $K_2HPO_4$ and $KH_2PO_4$, and the ratio of the two can be found in conventional method for DNA chip passivation and is not specifically defined herein. In one embodiment of the present application, reaction solutions are introduced into chip channels using a fluid device for reactions such as immobilization, weak passivation, and passivation. Conditions for passivation include 3-4 introductions of passivation reaction solution, a volume of 500 μL for each introduction, a flow rate of 1 mL/min, a time interval between introductions of 1800 s, and a temperature maintained at 37° C. during the passivation. The above conditions are for reference only and are not specifically defined herein.

The preparation method of the present application further comprises washing, wherein the washing comprises washing the passivated chip using three washing solutions in a sequence of RI-05, RI-06 and RI-07, with at least one washing for each washing solution, RI-05 being a PBS buffer, RI-06 being a mixture of HEPES buffer and NaCl solution, and RI-07 being double distilled water. Washing DNA chips after passivation is a known procedure in the art, and RI-05, RI-06 and RI-07 are conventional washing solutions. Generally, each washing solution requires 3 repetitions. HEPES refers to 4-(2-hydroxyethyl)-1-piperazineethanesulfonic acid.

In one embodiment of the present application, the passivation reaction solution contains at least one of the compounds of formula I as a small molecule modifier, formula I:

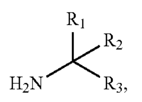

wherein, $R_1$, $R_2$ and $R_3$ are each independently selected from a hydrophilic group and a hydrogen atom.

According to the preparation method of the present application, the hydrophilic group is a negatively charged group or contains a negatively charged group. For example, the hydrophilic group contains a phosphate group, a phosphate ester group, a sulfonate group, a carboxylate group, a hydroxyl group, or an amide group.

In one embodiment of the present application, the compound of formula I is at least one of taurine, aminopropanesulfonic acid, serine, glutamic acid and phospho-serine.

In one embodiment of the present application, the anti-nonspecific adsorption layer is formed using a passivation reaction solution containing a small molecule modifier during the passivation.

Specifically, the concentration of the small molecule modifier in the passivation reaction solution is 0.01-0.2 mol/L.

It should be noted that the small molecule modifier in the passivation reaction solution is intended to bind to the substrate surface to form an anti-nonspecific adsorption layer. It will be appreciated that the anti-nonspecific adsorption layer can be formed by adding the small molecule modifier of the present application. To provide the layer with better nonspecific adsorption, the concentration of the small molecule modifier in the passivation reaction solution of the present application is optionally 0.01-0.2 mol/L. It will be appreciated that beyond this range, for example, a lower concentration may not be sufficient to form an effective anti-nonspecific adsorption layer, and a higher concentration may cause reagent waste and provide little improvement in nonspecific adsorption effect.

An accelerant is added into the passivation reaction solution to promote the binding reaction between the small molecule modifier and the substrate surface. The accelerant is at least one of benzyltriethylammonium chloride, phenyltrimethylammonium chloride and tetrabutylammonium chloride. The concentration of the accelerant in the passivation reaction solution is 10-50 mmol/L.

It should be noted that the accelerant is used to promote the binding reaction between the small molecule modifier and the substrate surface. With the action of the accelerant, the binding efficiency and quality of the small molecule modifier and the substrate surface are further improved, making the reaction more controllable and reproducible. Therefore, the passivation reaction solution in optional embodiments is further added with the accelerant. It will be appreciated that based on manufacturing or product design requirements, for example, a relatively lower demand on reaction controllability, the accelerant may not be used.

It should also be noted that benzyltriethylammonium chloride is only an exemplary accelerant that demonstrates applicability in one embodiment of the present application, and other accelerants are not excluded, as long as they are capable of promoting the binding reaction between the small molecule anti-nonspecific adsorption reagent and the substrate surface.

The preparation method of the present application further comprises performing weak passivation before passivation. The weak passivation comprises adding a small molecule modifier into weak passivation reaction solution to pre-immobilize the small molecule modifier on the substrate surface by the binding reaction between the small molecule modifier and the substrate surface.

It should be noted that one of the effects of the weak passivation is to pre-immobilize a small molecule modifier on the substrate surface by adding the small molecule modifier, before further enhancing the binding by the passivation to form a stable anti-nonspecific adsorption layer. In the weak passivation reaction solution, the concentration of the small molecule modifier is 15-45 mmol/L, preferably 30 mmol/L, and the condition is a 2- to 5-h incubation at 35-40° C.

In one embodiment of the present application, the small molecule modifier used in the weak passivation is the same as that used in the passivation.

Specifically, in one embodiment of the present application, the preparation method comprises weak passivation comprising contacting a weak passivation reaction solution containing a small molecule modifier or containing a small molecule modifier and a surfactant with a substrate to perform the weak passivation at a constant temperature. The weak passivation of the present application is intended to pre-immobilize the small molecule modifier to a substrate surface, and to adequately bind a DNA or protein to an epoxy group with the presence of the surfactant. It will be appreciated that the concentration of the small molecule modifier and the time for reaction will influence the amount of the small molecule modifier immobilized on the substrate surface. A higher concentration or a longer reaction time will result in a larger amount of immobilized small molecule modifier on the substrate surface. Similarly, a higher concentration of the surfactant or a longer reaction time will lead to a more adequate binding of the DNA or protein to the epoxy group. The specific properties can be determined according to manufacturing or product requirements, and are not specifically defined herein. In one embodiment of the present application, the weak passivation reaction solution is 0.25 mol/L $Na_2CO_3/NaHCO_3$ containing 10 nM surfactant and 30 mM small molecule modifier, pH 9.58-10.53. When the reaction solution is introduced into chip channels using a fluid device for weak passivation, the volume of the introduced solution is 1 mL, the flow rate is 1 mL/min, the reaction time is 3 h, and the reaction temperature is 37° C. The above conditions are for reference only and are not specifically defined herein.

The preparation method further comprises passivation, comprising washing the weakly passivated substrate using a passivation reaction solution, and contacting the passivation reaction solution containing a small molecule modifier or containing a small molecule modifier and accelerant with the washed substrate for passivation at a constant temperature. Generally, the passivation reaction solution is 1 mol/L $K_2HPO_4/KH_2PO_4$, pH 9.0, wherein $K_2HPO_4/KH_2PO_4$ refers to a passivation reaction solution composed of $K_2HPO_4$ and $KH_2PO_4$, and the ratio of the two can be found in conventional method for DNA chip passivation and is not specifically defined herein. Specifically, in one embodiment of the present application, 0.25 mol/L $Na_2CO_3/NaHCO_3$, pH 9.58-10.53 is used as the reaction solution containing the small molecule modifier or containing the small molecule modifier and the accelerant, and the concentration of the small molecule modifier is 0.01-0.2 M. When the reaction solution is introduced into chip channels using a fluid device for reaction, conditions for passivation include 3-4 introductions of passivation reaction solution, a volume of 500 μL for each introduction, a flow rate of 1 mL/min, a time interval between introductions of 1800 s, and a temperature maintained at 37° C. during the passivation. The above conditions are for reference only and are not specifically defined herein.

It should be noted that the novel small molecule compound of the present application is particularly suitable as a small molecule modifier for a DNA chip or a protein chip. As a small molecule modifier, the small molecule compound of the present application not only has the advantages of the existing small molecule modifier, but also features controllable reactions and good reproducibility, thus having important value for preparing DNA chips and protein chips of high availability for single-molecule detection. Therefore, the present application discloses a novel application of the small molecule compounds as small molecule modifiers for preparing DNA chips or protein chips, which forms an anti-nonspecific adsorption layer on a substrate surface.

In one embodiment of the present application, the preparation method of the present application comprises adding a protein into the immobilization reaction solution during DNA immobilization, such that the protein and the substrate surface are subjected to a binding reaction to immobilize the protein on the substrate surface, thereby achieving a protein co-modification effect.

It should be noted that, in one embodiment of the present application, the protein is immobilized on the substrate surface by a covalent bond, thereby solving the problem that the physical adsorption modification is easily desorbed. As to the means to form the covalent bond, any conventional method for forming a covalent bond can be used. For example, the protein can be immobilized on the substrate surface by a covalent bond formed by the reaction between an amino group of the protein and a modified epoxy group on the substrate surface, which depends on the manufacturing conditions and is not specifically defined herein.

It should also be noted that, in general, a method for preparing a DNA chip comprises procedures such as immobilization, passivation and washing. The present application includes adding a protein into the immobilization reaction solution during immobilization for a reaction between the protein and the substrate surface to immobilize the protein on the substrate surface. For other steps, such as passivation and subsequent washing, the existing preparation process of DNA chips can be used, and the substrate can also be an existing substrate that is used conventionally, and is not specifically defined herein.

In one embodiment of the present application, the protein used in the preparation method is bovine serum albumin (BSA).

In one embodiment of the present application, the substrate surface has an epoxy silane modification. It should be noted that the substrate surface is modified by epoxy silane, such that the protein can be immobilized on the substrate surface through a covalent bond formed by the reaction between the amino group of the protein and the epoxy silane modification, and the protein can be stably and effectively immobilized on the substrate surface.

The method further comprises passivation after the immobilization, and sulfydryl blocking on the passivated substrate after the passivation to block sulfydryl groups on the protein immobilized on the substrate surface.

It should be noted that, both the physisorbed protein and the covalently immobilized protein in the embodiments of the present application have a problem of nonspecific adsorption of small molecules, particularly, small molecules containing sulfydryl groups. Among these, non-specific adsorption of sulfydryl-containing small molecules is caused in part by the introduction of sulfydryl groups on the protein as co-modification. Based on the above knowledge, the present application creatively proposes the addition of sulfydryl blocking after passivation to block sulfydryl groups on the protein immobilized on the substrate surface, thus reducing or even avoiding the nonspecific adsorption of sulfydryl-containing small molecule substances such as cysteine (Cys), homocysteine (Hey), reduced glutathione (GSH) and sulfydryl-containing nucleotide molecules on the protein co-modification DNA chip. Moreover, when the sulfydryl groups are blocked, more hydrophilic groups or negatively charged groups can be introduced on the surface of the protein co-modified DNA chip, such that the nonspecific adsorption resistance of the DNA chip is further enhanced. It will be appreciated that the present application includes unexpectedly propose the blocking of sulfydryl groups on the co-modified protein to inactivate the sulfydryl groups on the protein. For the specific sulfydryl blocking method, reference may be made to conventional methods for protein sulfydryl blocking or the sulfydryl group on the protein may be inactivated by reaction with the sulfydryl group using any existing technology, which is not specifically defined herein.

It will be appreciated by those skilled in the art that nucleotides in this application refer to nucleosides, nucleotides and their analogs and derivatives, and that they do not alter the Watson-Crick base pairing function of nucleosides and nucleotides.

In one embodiment of the present application, the sulfydryl blocking specifically comprises reducing a disulfide bond in the protein with a reductant to form a reductive sulfydryl group, and blocking the formed reductive sulfydryl group with a sulfydryl blocking reagent. The reductant used is at least one of tris(2-carboxyethyl)phosphine (TCEP), tris(3-hydroxypropyl)phosphine (THPP), dithiothreitol (DTT) and mercaptoethanol (ME). The sulfydryl blocking reagent used is at least one of iodoacetamide, iodoacetic acid, maleimide and epoxy propanol.

The preparation method of the present application further comprises performing weak passivation after DNA immobilization and before passivation, comprising adding a catalyst and a protein into the reaction solution to promote the binding of the DNA and the protein to the substrate surface to ensure that the DNA and the protein are adequately immobilized on the substrate surface.

It should be noted that the weak passivation is to promote the binding of DNA and protein to the substrate surface by using a catalyst, such that the amount of DNA or protein bound to the substrate surface has better dependence and correspondence with the initial concentration of DNA or protein, thereby making the quality of DNA or protein immobilized on the DNA chip controllable and improving the quality and effect of protein co-modification. It will be appreciated that an inadequate binding of DNA or protein to the substrate surface may lead to an unstable amount of DNA or protein bound to DNA chips of the same or different batches, which do not satisfy the production and use requirements of highly available DNA chips. By adding the procedure of weak passivation and using the catalyst in the weak passivation, the DNA and the protein can be efficiently and adequately bound to the substrate, demonstrating good reproducibility and controllable amount of immobilized DNA and protein.

In one embodiment of the present application, the preparation method specifically comprises the following steps:

immobilization, comprising contacting a immobilization reaction solution containing a DNA and protein with the substrate surface for immobilization at a constant temperature, wherein in general, the immobilization reaction solution is 0.25 mol/L $Na_2CO_3/NaHCO_3$, pH 9.78, the concentration of DNA is generally 0.01-0.4 nmol/L, the concentration of protein is generally 10-100 μmol/L, the temperature of immobilization is about 37° C., the time for immobilization is about 30 min, and the above conditions are for reference only and are not specifically defined herein; the "$Na_2CO_3/NaHCO_3$" refers to an immobilization reaction solution composed of $Na_2CO_3$ and $NaHCO_3$, and the ratio of the two can be found in conventional method for DNA chip immobilization and is not specifically defined herein;

weak passivation, comprising contacting a weak passivation reaction solution containing a catalyst and a protein or containing a catalyst, a small molecule modifier and a protein with a substrate for the weak passivation at a constant temperature, wherein the small molecule modifier can be immobilized to a substrate surface to form an anti-nonspecific adsorption layer, and the catalyst, especially a surfactant, adequately binds the DNA or protein to a modified group on the substrate surface; it will be appreciated that the concentration of the small molecule modifier and the time for reaction will influence the amount of the small molecule modifier immobilized on the substrate surface; a higher concentration or a longer reaction time will result in a larger amount of immobilized small molecule modifier on the substrate surface, and similarly, a higher concentration of the surfactant or a longer reaction time will lead to a more adequate binding of the DNA or protein to the modified group on the substrate surface; the specific properties can be determined according to manufacturing or product requirements, and are not specifically defined herein; in one embodiment of the present application, the weak passivation reaction solution is 0.25 mol/L $Na_2CO_3/NaHCO_3$ containing 10 nM surfactant, 30 mM small-molecule modifier and 10-100 μM protein, pH 9.58-10.53; when the reaction solution is introduced into chip channels using a fluid device for weak passivation, the volume of the introduced solution is 1 mL, the flow rate is 1 mL/min, the reaction time is 3 h, and the reaction temperature is 37° C. The above conditions are for reference only and are not specifically defined herein;

passivation, comprising washing the weakly passivated substrate using passivation reaction solution, and contacting the passivation reaction solution with the weakly passivated substrate surface for passivation at a constant temperature, wherein generally, the passivation reaction solution is 1 mol/L $K_2HPO_4/KH_2PO_4$, pH 9.0, $K_2HPO_4/KH_2PO_4$ refers to a passivation reaction solution composed of $K_2HPO_4$ and $KH_2PO_4$, and the ratio of the two can be found in conventional method for DNA chip passivation and is not specifically defined herein; in one embodiment of the present application, reaction solutions are introduced into chip channels using a fluid device for reactions such as immobilization, weak passivation, and passivation; conditions for passivation include 3-4 introductions of passivation reaction solution, a volume of 500 μL for each introduction, a flow rate of 1 mL/min, a time interval between introductions of 1800 s, and a temperature maintained at 37° C. during the passivation; the above conditions are for reference only and are not specifically defined herein;

sulfydryl blocking, comprising reducing a disulfide bond in the adsorbed protein on the passivated substrate with a reductant to form a reductive sulfydryl group, and blocking the formed reductive sulfydryl group with a sulfydryl blocking reagent; the purpose of the sulfydryl blocking is to block free sulfydryl groups on the protein; it will be appreciated that all existing methods that can block free sulfydryl groups on proteins can be used for reference in this application; in one embodiment of the present application, a fluid device is used for introducing reaction solutions into chip channels for reaction; the sulfydryl blocking comprises introducing a reduction reaction solution containing a reductant, which is a mixture of 150 mM Tris pH8.0, 100 mM NaCl and 30 mM reductant, with a volume of 1 mL, a flow rate of 1 mL/min, a reaction time of 10-30 min and a reaction temperature of 37° C., and introducing a blocking reaction solution containing a sulfydryl blocking reagent, which contains 150 mM HEPES pH 8.5, 100 mM NaCl and 30 mM sulfydryl blocking reagent, with a volume of 1 mL, a flow rate of 1 mL/min, a reaction time of 10-30 min and a reaction temperature of 37° C.; the above conditions are for reference and are not specifically defined herein; and washing the obtained DNA chip, comprising washing the passivated substrate using three washing solutions in a sequence of RI-05, RI-06 and RI-07, with at least one washing for each washing solution, wherein RI-05 is a phosphate buffer, RI-06 is a mixture of HEPES buffer and NaCl solution, and RI-07 is double distilled water. Washing DNA chips after passivation is a known procedure in the art, and RI-05, RI-06 and RI-07 are conventional washing solutions. Generally, each washing solution requires 3 repetitions. HEPES refers to 4-(2-hydroxyethyl)-1-piperazineethanesulfonic acid.

The present application also discloses a DNA or protein chip prepared by the method for preparing the same.

It should be noted that, on one hand, the DNA or protein chip of the present application has higher binding efficiency and quality between DNA or protein and substrate, and can effectively ensure the performance of DNA or protein chip; on the other hand, the amount of the DNA or protein immobilized on the DNA or protein chip is highly controllable, with good reproducibility, satisfying the customization demand of the DNA or protein chips in different tests. The DNA or protein chip modified by small molecules can reduce the nonspecific adsorption of nucleotide and improve the ratio of characteristic detection signals. The DNA or protein chip with protein modification can reduce the nonspecific adsorption of proteins, especially polymerase.

According to one aspect of the present application, a substrate comprising a surface is provided, the surface comprised in the substrate is also called the substrate surface. The surface immobilized with one or more oligonucleotides and coated with an anti-nonspecific adsorption layer, the anti-nonspecific adsorption layer comprising a small molecule modifier selected at least one from the compounds having a structural formula I, (I)

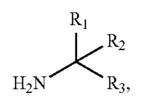

wherein $R_1$, $R_2$ and $R_3$ are each independently selected from a hydrophilic group or a hydrogen atom. A chip comprises the substrate is also called a DNA chip.

In an embodiment, the hydrophilic group is a negatively charged group.

In an embodiment, the hydrophilic group comprises a phosphate group, a phosphate ester group, a sulfonate group, a carboxylate group, a hydroxyl group, or an amide group.

In an embodiment, the small molecule modifier is selected at least one member from taurine, aminopropanesulfonic acid, serine, glutamic acid and phospho-serine.

In an embodiment, the surface is a chemical modified surface, the surface comprises an active group selected at least one from epoxy group, formyl, carboxyl, N-hydroxysuccinimide and diaminobenzanilide.

In an embodiment, the small molecule modifier is covalently attached to the surface.

In an embodiment, the surface immobilized with oligonucleotides and protein molecules.

Oligonucleotide here is also called primer or probe, is a known nucleic acid sequence usually less than 200 nt, less than 100 nt, or less than 50 nt. Oligonucleotides are usually designed to hybridize with at least a portion of the template or target nucleic acid.

In an embodiment, sulfydryl groups on the protein molecules are blocked.

In an embodiment, methods of making the substrate as any of the embodiments above are provided, the method comprising (a) providing a solid support comprising a surface; (b) immobilizing one or more oligonucleotides to the surface; and (c) performing a weak passivation on the surface, wherein the weak passivation comprising contacting a weak passivation reaction solution containing a small molecule modifier selected at least one from the compounds having a structural formula I with the surface, (I)

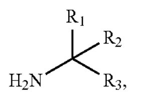

wherein $R_1$, $R_2$ and $R_3$ are each independently selected from a hydrophilic group or a hydrogen atom.

In an embodiment, the hydrophilic group is a negatively charged group.

In an embodiment, the hydrophilic group comprises a phosphate group, a phosphate ester group, a sulfonate group, a carboxylate group, a hydroxyl group, or an amide group.

In an embodiment, the small molecule modifier is selected at least one from taurine, aminopropanesulfonic acid, serine, glutamic acid and phospho-serine.

In an embodiment, the surface is a chemical modified surface, wherein the surface comprising an active group selected at least one from epoxy group, formyl, carboxyl, N-hydroxysuccinimide and diaminobenzanilide.

In an embodiment, the weak passivation reaction solution further comprises a surfactant.

In an embodiment, the surfactant is selected at least one from cetyltrimethylammonium bromide, dioctadecylammonium bromide, cetyltrimethylammonium chloride, dodecyltrimethylammonium bromide and tetraoctylammonium bromide.

In an embodiment, (b) comprises contacting an immobilization reaction solution containing the oligonucleotides with the surface to immobilize the oligonucleotides, the immobilization reaction solution comprising a surfactant, wherein the surfactant is selected at least one from cetyltrimethylammonium bromide, dioctadecylammonium bromide, cetyltrimethylammonium chloride, dodecyltrimethylammonium bromide and tetraoctylammonium bromide.

In an embodiment, (b) comprises contacting an immobilization reaction solution containing the oligonucleotides and one or more protein molecules with the surface to immobilize the oligonucleotides and the protein molecules, wherein sulfydryl groups on the protein molecules are blocked.

In an embodiment, the method further comprises (d) performing a passivation on the surface, the passivation comprising contacting a passivation reaction solution with the surface, wherein the passivation reaction solution comprises a small molecule modifier selected at least one from the compounds having the structural formula I.

In an embodiment, the small molecule modifier is the same as that in the weak passivation reaction solution. The DNA chip or the protein chip has a substrate surface provided with an anti-nonspecific adsorption layer formed by binding a small molecule modifier on the substrate surface, wherein the small molecule modifier is at least one of the compounds of formula I; formula I:

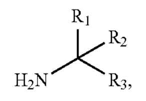

$R_1$, $R_2$ and $R_3$ are each independently selected from a hydrophilic group and a hydrogen atom.

It should be noted that the chip of the present application features using a compound of formula I as the small molecule modifier to form the anti-nonspecific adsorption layer of the chip.

Compared with the existing small molecule modifier, the small molecule modifier of the present application has the advantages of good controllability, good reproducibility and accurate control of nonspecific adsorption, thereby acquiring a highly-available DNA chip or protein chip for single molecule detection. The small molecule modifier of the present application refers to a small molecule compound having a relative molecular mass of 1000 or less.

According to one embodiment of the present application, in the compound of formula I, the hydrophilic group is a negatively charged group or contains a negatively charged group. For example, the hydrophilic group contains a phosphate group, a phosphate ester group, a sulfonate group, a carboxylate group, a hydroxyl group, or an amide group. Specifically, the compound of formula I is at least one of taurine, aminopropanesulfonic acid, serine, glutamic acid and phospho-serine.

The substrate surface of the chip of the present application has an epoxy silane modification. It will be appreciated that binding of the small molecule modifier to the substrate surface may be covalent or non-covalent. In one embodiment of the present application, the small molecule modifier binds to the substrate surface via a covalent bond, thereby forming a stable and controllable anti-nonspecific adsorption layer.

In one embodiment of the present application, the DNA chip is formed by binding the protein to the substrate surface of the DNA chip.

It will be appreciated that the protein can bind to the substrate surface of the DNA chip by a covalent bond or non-covalent bond. In one embodiment of the present application, the protein binds to the substrate surface of the DNA chip by a covalent bond to firmly immobilize the protein on the substrate surface, and the covalent bond immobilizes the protein more firmly than physical adsorption modification, avoids desorption, and further avoids non-specific adsorption due to desorption during the use of the protein co-modified DNA chip. For example, in sequencing or detection and identification, the protein co-modified DNA chip of the present application can avoid the adsorption of enzyme and the adsorption of nucleotide in the sequencing process due to desorption of protein.

According to one embodiment of the present application, in the protein co-modification DNA chip, the protein used for protein co-modification is bovine serum albumin.

In one embodiment of the present application, the sulfydryl group on the co-modification protein is in a blocked state. It should be noted that, as the sulfydryl group on the protein is in a blocked state, the protein co-modification DNA chip of the present application reduces or even avoids the adsorption of molecules containing sulfydryl group, and has the function of resisting adsorption of molecules containing sulfydryl group. In addition, in one embodiment of the present application, when the sulfydryl group is blocked, more hydrophilic groups or negatively charged groups are introduced by the adopted blocking reagent, such that the nonspecific adsorption resistance of the DNA chip is further enhanced.

According to one embodiment of the present application, in the protein co-modified DNA chip of the present application, the substrate surface has an anti-nonspecific adsorption layer formed by a small molecule modifier. The small molecule modifier of the present application refers to a small molecule compound having a relative molecular mass of 1000 or less. The small molecule modifier is at least one of taurine, aminopropanesulfonic acid, serine, glutamic acid and phospho-serine.

It will be appreciated that binding of the small molecule modifier to the substrate surface may be covalent or non-covalent. In one embodiment of the present application, the small molecule modifier binds to the substrate surface via a covalent bond, thereby forming a stable and controllable anti-nonspecific adsorption layer.

It should be noted that in addition to the protein co-modification, the protein co-modified DNA chip of the present application further employs a conventional small molecule modifier to form the anti-nonspecific adsorption layer, thereby further improving the nonspecific adsorption resistance of the DNA chip. Particularly, in a preferred embodiment of the present application, small molecule modifiers with good controllability and reproducibility such as taurine, aminopropanesulfonic acid, serine, glutamic acid and phospho-serine are disclosed, such that the preparation of the anti-nonspecific adsorption layer is highly controllable. They can effectively act on the substrate surface with the protein co-modification, thus enhancing the non-specific adsorption resistance of the DNA chip.

In another aspect, the present application discloses the use of the DNA or protein chip prepared by the preparation method of the present application in nucleic acid or protein assay and analysis.

Among them, the nucleic acid or protein assay includes sequencing, hybridization assay, immunoassay, SNP analysis, and the like.

In one embodiment, a method of detecting nucleic acids is provided, the method comprises (a) providing a solid support comprising a surface and a library of target nucleic acids, the surface immobilized with one or more oligonucleotides and coated with an anti-nonspecific adsorption layer, the anti-nonspecific adsorption layer comprising a small molecule modifier selected at least one from the compounds having a structural formula I, (I)

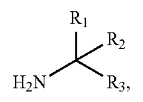

wherein $R_1$, $R_2$ and $R_3$ are each independently selected from a hydrophilic group or a hydrogen atom; (b) hybridizing the target nucleic acids with the oligonucleotides on the surface; and (c) detecting the solid support to identify the target nucleic acids that binds to the oligonucleotides.

According to still another aspect of the present application, a method for immobilizing a DNA or protein is disclosed, comprising: performing weak passivation after immobilizing the DNA or protein, comprising contacting a weak passivation reaction solution with a substrate surface after immobilization to promote the binding of the DNA or protein to the substrate surface, such that the DNA or protein is adequately immobilized on the substrate surface, wherein the weak passivation reaction solution contains a catalyst that promotes the binding of the DNA or protein to the substrate surface, thereby adequately immobilizing the DNA or protein on the substrate surface.

In one embodiment of the present application, in the method for immobilizing a DNA or protein of the present application, the catalyst is a surfactant. Preferably, the surfactant is at least one of cetyltrimethylammonium bromide, dioctadecylammonium bromide, cetyltrimethylammonium chloride, dodecyltrimethylammonium bromide and tetraoctylammonium bromide.

It should be noted that one of the method for preparing a DNA or protein chip of the present application includes a weak passivation procedure, using a catalyst to generate a more adequate covalent bonding of the DNA or protein to the substrate surface. It will be appreciated that the method for preparing a DNA or protein chip of the present application may also be referred to in other cases where a DNA or protein is required to be immobilized on a carrier. Therefore, the present application particularly provides a method for immobilizing a DNA or protein, which is not only suitable for immobilizing the DNA or protein on a chip substrate, but also suitable for other cases where a DNA or protein is immobilized on a carrier through a covalent bond, for example, immobilizing the DNA or protein on a microsphere carrier or other types of carriers according to the requirements of use or product, which is not specifically defined herein.

In one embodiment of the present application, an immobilization reaction solution used in the method for preparing a DNA or protein chip of the present application contains a protein. The protein used is preferably bovine serum albumin.

The method for preparing a DNA or protein chip of the present application further comprises passivation, which comprises using a passivation reaction solution that contains at least one of compounds of general formula I as a small molecule modifier.

In one embodiment of the present application, the weak passivation reaction solution contains at least one of the compounds of general formula I as a small molecule modifier.

In one embodiment of the present application, the method for immobilizing further comprises sulfydryl blocking, which blocks a sulfydryl group on a protein immobilized on a substrate. The sulfydryl blocking specifically comprises reducing a disulfide bond in the protein with a reductant to form a reductive sulfydryl group, and blocking the formed reductive sulfydryl group with a sulfydryl blocking reagent. The sulfydryl reductant is at least one of tri(2-carboxyethyl) phosphine, tri(3-hydroxypropyl)phosphine, dithiothreitol and mercaptoethanol. The sulfydryl blocking reagent is at least one of iodoacetamide, iodoacetic acid, maleimide and epoxy propanol.

It should be noted that the DNA chip or protein chip in the present application refers to a chip having a DNA or protein immobilized on a substrate surface. In the present application, unless otherwise the type of a DNA or protein is specifically indicated, the DNA refers to a substance containing a DNA sequence or an amino acid sequence, for example, a DNA immobilized on a DNA chip may contain a nucleotide derivative, a nucleotide analogue, a fluorescent label, or both a nucleotide sequence and an amino acid sequence; and the protein refers to a substance containing an amino acid sequence.

It should be noted that the chip substrate surface in the present application has a chemical modification, that is, the surface is a chemically modified surface, which contains an active group capable of reacting with a DNA or protein, and the DNA or protein is immobilized on a substrate surface by the reaction between the active group and the DNA or protein.

The beneficial effects of technical solutions provided by this application include but are not limited to the following:

1. In the method for preparing a DNA or protein chip of the present application, a weak passivation procedure is creatively added, in which a catalyst is used to generate a more adequate binding of a DNA or protein to a substrate surface, such that the DNA can be adequately immobilized on the substrate surface. As such, not only are the quality and efficiency of the DNA or protein immobilization improved, but also the amount of the DNA or protein immobilized on the DNA or protein chip can be highly controllable and has good reproducibility, laying a foundation for preparing DNA or protein chips of high quality and high availability.

2. The biochip of the present application contains the compound of formula I as a small molecule modifier to form an anti-nonspecific adsorption layer of the biochip. The layer can effectively resist the nonspecific adsorption of nucleotides used for sequencing, improves the ratio of specific detection signals, and reduces the interference of nonspecific signals, and has advantages such as high binding strength and difficult shedding. Moreover, the small molecule modifier of the present application has controllable reaction and good reproductively, so that the biochip of the present application has high quality, good reproductively and high availability, and is particularly suitable for single molecule detection.

3. The protein co-modified DNA chip binds to the protein on the substrate surface, having the advantages such as easy operations, wide raw material sources, good effects and low comprehensive costs, and immobilizes the protein through a covalent bond in an embodiment, which strengthens the immobilization and reduces the tendency to desorb, thereby avoiding nonspecific adsorption caused by the desorption.

In one embodiment of the present application, the nonspecific adsorption resistance of the protein co-modified DNA chip to sulfydryl-containing molecules is further enhanced by blocking sulfydryl on the co-modified protein.

In addition, when the sulfydryl is blocked, more hydrophilic groups or negatively charged groups are introduced into the adopted blocking reagent, so that the nonspecific adsorption resistance of the DNA chip is further enhanced.

In another embodiment, a weak passivation procedure is added in the method for preparing a protein co-modified DNA chip of the present application, in which a catalyst, particularly a surfactant, is used to promote a more complete reaction between the DNA and protein and a modified group, such that the DNA is effectively immobilized on the substrate. As such, not only are the quality and efficiency of the DNA immobilization improved, improving the protein co-modification effect, but also the amount of the DNA immobilized on the DNA chip can be highly controllable and has good reproductively.

In another improvement scheme of the present application, a small molecule modifier is added in the weak passivation procedure, and the nonspecific adsorption resistance effect of the DNA chip is further enhanced by utilizing the efficient and controllable adsorption and immobilization of the substrate to the small molecule modifier.

DETAILED DESCRIPTION

Immobilizing a DNA to a substrate via a covalent bond is an existing technique for preparing a DNA chip. However, studies have shown that generating a more adequate covalent bonding of DNA with a substrate surface is the key to affect DNA immobilization, and stability and reproducibility of DNA chip production directly. For example, based on the principle of immobilizing a DNA through a covalent bond generated by an amino group of the DNA and an epoxy group on a substrate surface, the DNA chip produced at present has poor reproductively, and poor applicability due to the poor consistency of the amount of DNA immobilized in different batches or even the same batch of DNA chips. Therefore, how to control the amount of DNA immobilized and improve the stability and reproducibility of DNA chips has been the focus of research in the art.

Based on the above knowledge, the present application creatively proposes that a weak passivation procedure is added after immobilization, in which a catalyst is used to generate a more adequate covalent bonding of a DNA with a substrate surface, such that the DNA is immobilized on the substrate more effectively. As such, not only are the efficiency and quality of the DNA immobilization on the substrate surface are improved, but also the amount of the DNA immobilized on the DNA chip correlates well with the concentration of the DNA added in the immobilization reaction solution, such that the amount of the DNA immobilized on the DNA chip can be controlled and has good reproducibility. This lays a foundation for preparing DNA chips of high quality, and meets the requirement of customized production. The scheme is applicable not only to the immobilization of a DNA on a substrate surface but also to a protein chip with similar conditions.

Figures 1, 2, 3, 4, 5, 6:
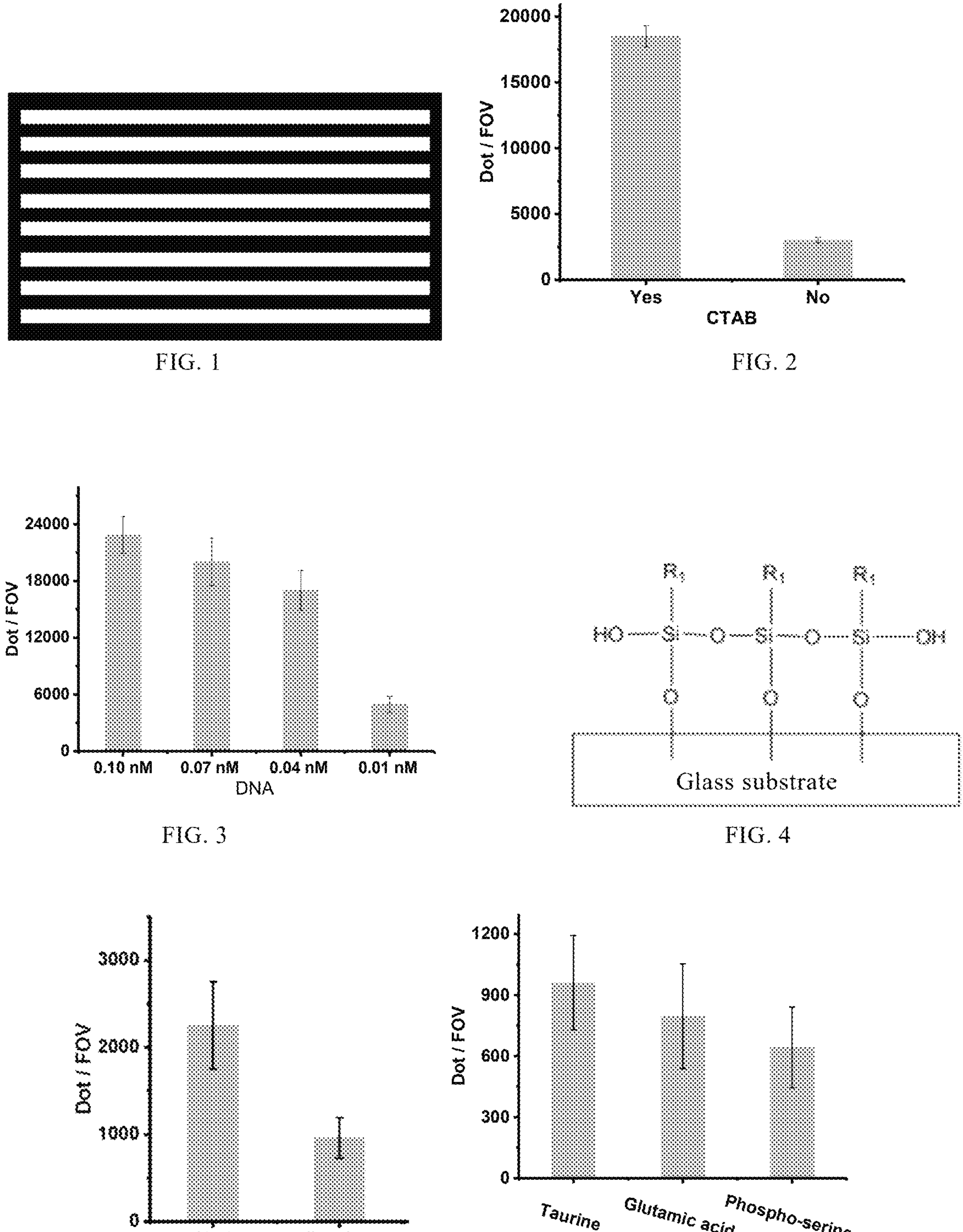
FIG. 1 is a structural schematic of a chip substrate.
FIG. 2 is a graph showing the results of the immobilized density assay on different weakly passivated DNA chips in Examples 1 and 2 of the present application.
FIG. 3 is a graph showing the results of the immobilized density assay on the DNA chips obtained at different initial DNA concentrations in Example II of the present application.
FIG. 4 is a structural schematic showing a glass substrate in Examples I to XII of the present application.
FIG. 5 is a graph showing the results of the nonspecific adsorption experiment on the chip added with a small molecule taurine having a single negatively charged group and the chip without a small molecule modifier in Example III of the present application.
FIG. 6 is a graph showing the results of the nonspecific adsorption experiment on the chip added with small molecules glutamic acid and phospho-serine having multiple negatively charged groups and the chip added with a small molecule having a single negatively charged group in Example IV of the present application.

In one embodiment of the present application, an amino group of a DNA or protein reacts with an active group on a substrate surface. The structure of chemical modification on the substrate surface is shown in FIG. 4, wherein $R_1$ represents an alkane chain molecule with an active group connected to the terminus, wherein the active group is preferably at least one of epoxy group, formyl, carboxyl, N-hydroxysuccinimide and diaminobenzanilide. The catalyst of the present application can promote the reaction between the amino group of DNA and the active group of chemical modification shown in FIG. 4 to form a covalent bond, such that the DNA is adequately immobilized on the substrate surface.

Meanwhile, the nonspecific adsorption of the chip directly affects the quantity and ratio of the effective sequencing data. The nonspecific adsorption can be reduced by a variety of methods. At present, forming an anti-nonspecific adsorption layer through the specific small molecule modification is an existing technique, and the small molecule anti-nonspecific adsorption layer is widely used due to its obvious advantages such as high binding strength, difficult shedding, and nonspecific adsorption resistance of a broader spectrum. However, problems such as poor controllability and weak reproducibility are common in the existing small molecule modifications, so that the different batches or even the same batch of small molecule modifications have different adsorption resistance effects, and therefore, it is difficult to stably and reliably prepare single-molecule-detected DNA chips and protein chips of high availability.

In the present application, in a large number of long-term studies of DNA chips and protein chips, the small molecule modifiers of general formula I such as taurine, aminopropanesulfonic acid, serine, glutamic acid, and phospho-serine are found to have highly efficient and controllable binding ability to a substrate. In addition, the small molecule modifiers of the present application have good reproducibility in binding to the substrate, can stably and reliably prepare highly available DNA chips or protein chips with good nonspecific adsorption resistance effect, and are particularly suitable for single molecule detection.

In a further improvement scheme of the present application, the present application further creatively proposes that a surfactant is introduced during the preparation of a DNA chip or protein chip to enable the DNA or protein to be more effectively immobilized on the substrate, based on the principle that a surfactant enables a DNA or protein to react more completely with a modified group on a substrate surface. The DNA or protein reacts more completely with the modified group on the substrate surface when a surfactant is used. As such, not only are the efficiency and quality of the DNA or protein immobilized on the substrate surface improved, but also the amount of the DNA or protein immobilized on the biochip correlates well with the concentration of the DNA or protein initially added in the immobilization reaction solution, such that the quality of the DNA or protein immobilized on the biochip can be controlled, and has good reproductivity. This lays a foundation for preparing biochips of high quality, and meets the requirement of customized production.

It should be noted that the chip substrate surface in the present application has chemical modifications, which contain active groups capable of reacting with DNA or proteins. In one embodiment of the present application, an amino group of a DNA or protein reacts with an active group that is one of epoxy group, formyl, carboxyl, N-hydroxysuccinimide and diaminobenzanilide.

In one embodiment of the present application, the modified structure on the substrate surface is shown in FIG. 4, where $R_1$ represents an alkane chain molecule with an active group connected to the terminus, wherein the active group is preferably at least one of epoxy group, formyl, carboxyl, N-hydroxysuccinimide and diaminobenzanilide.

In one embodiment of the present application, the chemical modification on the substrate surface can bind to the small molecule modifier of the present application, such that the small molecule modifier is immobilized on the substrate surface to form an anti-nonspecific adsorption layer.

Another method for reducing the nonspecific adsorption of the chip is protein modification. For existing protein co-modified DNA chips, proteins are immobilized on a substrate surface mainly by using a physical adsorption to resist the protein adsorption. However, the physical adsorption is weak and easy to desorb. In this regard, the present application creatively proposes that the protein is immobilized on the substrate surface through a covalent bond, which not only strengthens the immobilization but also reduces the desorption, thereby avoiding nonspecific adsorption signals caused by the desorption.

In one embodiment of the present application, an amino group of a DNA reacts with an active group on a substrate surface. The structure of chemical modification on the substrate surface is shown in FIG. 4, wherein $R_1$ represents an alkane chain molecule with an active group connected to the terminus, wherein the active group is preferably at least one of epoxy group, formyl, carboxyl, N-hydroxysuccinimide and diaminobenzanilide. The catalyst of the present application can promote the reaction between the amino group of DNA and the active group shown in FIG. 4 to form a covalent bond, such that the DNA is adequately immobilized on the substrate surface.

In addition, it has been found that existing protein co-modified DNA chips have higher adsorption of small molecules such as cysteine (Cys), homocysteine (Hey), reduced glutathione (GSH) and sulfydryl-containing nucleotide molecules, and that a co-modified protein as a blocking reagent has a large amount of free sulfydryl, so that sulfydryl-containing small molecules containing such as cysteine can be nonspecifically adsorbed. Based on the above knowledge, the present application creatively proposes that the sulfydryl blocking is performed on the passivated substrate to block the free sulfydryl of the protein on the substrate, thereby reducing or even avoiding the adsorption of the sulfydryl-containing small molecules by the protein co-modified DNA chip, and reducing the nonspecific signals of the DNA chip.

In a further improvement scheme of the present application, the present application further creatively proposes that a weak passivation procedure using a surfactant is introduced during the preparation of a DNA chip or protein chip, that is after the immobilization the DNA or protein, to enable the DNA or protein to be more effectively immobilized on the substrate, based on the principle that a catalyst (particularly a surfactant) enables a DNA or protein to react more completely with a modified group on a substrate surface. The DNA or protein reacts more completely with the modified group on the substrate surface when a surfactant is used. As such, not only are the efficiency and quality of the DNA or protein immobilized on the substrate surface improved, but also the amount of the DNA or protein immobilized on the biochip correlates well with the concentration of the DNA or protein initially added in the immobilization reaction solution, such that the quality of the DNA or protein immobilized on the biochip can be controlled, and has good reproductivity. This lays a foundation for preparing biochips of high quality, and meets the requirement of customized production.

In a further improvement scheme of the present application, a small molecule modifier is added in the weak passivation procedure, and the small molecule modifier is immobilized on a substrate, so that the nonspecific adsorption of the DNA chip is further reduced. In addition, the small molecule modifiers such as taurine, aminopropanesulfonic acid, serine, glutamic acid and phospho-serine have highly efficient and controllable binding ability to an epoxy group of the substrate, and the small molecule modifiers have good reproducibility in binding to the substrate, so that the problems of poor controllability and weak reproducibility of the existing small molecule modifiers are solved, and highly available DNA chips with good nonspecific adsorption resistance effect can be stably and reliably prepared.

Some of the terms involved in the embodiments of the present application are explained below:

Weak passivation: in the present application, the weak passivation is an intermediate procedure between the immobilization and passivation procedures, aiming to further promote the reaction between the DNA and the chip substrate surface using CTAB at a high concentration.

Passivation: inactivating the active groups by a certain method. In the present application, the epoxy group of the epoxy-modified chip undergoes a ring-opening reaction in $K_2HPO_4/KH_2PO_4$ solution.

AT-01: 0.25 M $Na_2CO_3/NaHCO_3$ containing 0.6 mM CTAB, pH 9.78;

RI-04: 1 M $K_2HPO_4/KH_2PO_4$, pH 9.0;

RI-05: PBS solution, pH 7.4;

RI-06: a mixture of 150 mM HEPES buffer and 150 mM NaCl solution;

RI-07: double distilled water;

Dot/FOV: the number of dots/spots observed in a field of view (region) of 110×110 μm.

The present application will be described in further detail with reference to specific examples. The following examples are merely illustrative of the present application and should not be construed as defining the present application. The examples without a specified particular technique or condition are performed in accordance with techniques or conditions described in literatures in the art or in accordance with the product specification. The reagents or instruments not provided with manufacturer are conventional and commercially available products.

Example I

In this example, a DNA chip was prepared by immobilizing a DNA, through an amino group of the DNA, on a glass substrate having epoxy silane on the surface thereof. In the preparation process, a weak passivation procedure was added after the immobilization, and a surfactant CTAB was used as the catalyst of this example. In this example, the effects of adding CTAB or not on DNA immobilization during the weak passivation were compared.

In this example, the DNA was immobilized on the chip substrate by "in-channel" immobilization, specifically, the chip substrate was packaged, and then various reagents and detergents are introduced into the packaged chip channels by using a fluid device, such that chemical reactions such as immobilization and passivation were performed. As shown in FIG. 1, independent chip channels were formed in the packaged chip substrate, and each chip channel could independently perform the reactions. FIG. 1 shows a packaged chip substrate with 8 independent chip channels with the specification of 90 mm×1.8 mm×0.1 mm in length×width×height. The chip substrate can be packaged into 16 channels according to different packaging processes or fluid devices as well, and 16 kinds of DNAs with different modifications can be independently prepared on one DNA chip.

The procedures for preparing the DNA chip of this example are as follows:

(1) Immobilization: an immobilization reaction solution AT-01 containing 0.05 nM DNA (50 deoxythymidine monophosphates) was introduced into channels of the chip substrate for the immobilization, wherein the 5' end of the contained DNA had both an amino modification $NH_2$ and a Cy3 fluorophore modification; AT-01 was 0.25 M $Na_2CO_3/NaHCO_3$ containing 0.6 mM CTAB, pH 9.78, the volume of the introduced solution was 1 mL, the flow rate was 1 mL/min, the reaction time was 30 min, and the reaction temperature was 37° C.;

(2) Weak passivation: a weak passivation reaction solution was introduced for the "weak passivation", wherein the weak passivation reaction solution was 0.25 M $Na_2CO_3/NaHCO_3$ containing 10 mM CTAB, pH 9.58-10.53, specifically pH 9.78 in this example;

compared with Example II, in this example, the weak passivation reaction solution was introduced into one half of the channels, and the weak passivation reaction solution 0.25 M $Na_2CO_3/NaHCO_3$ containing no CTAB, pH 9.78 was introduced into the other half of the channels;

for all channels, the volume of the introduced solution was set to 1 mL, the flow rate was set to 1 mL/min, the reaction time was set to 3 h, and the reaction temperature was set to 37° C.;

(3) Washing away the weak passivation reaction solution: a passivation reaction solution RI-04 was introduced for washing for 3 times, wherein the volume introduced each time was 1 mL, the flow rate was 1 mL/min, and the temperature was maintained at 37° C. during the washing; RI-04 was 1 M $K_2HPO_4/KH_2PO_4$, pH 9.0;

(4) Passivation: a passivation reaction solution RI-04 was introduced for washing for 3-4 times, wherein the volume introduced each time was 500 L, the flow rate was 1 mL/min, the time interval between introductions was 1800 s, and the temperature was maintained at 37° C. during the passivation; RI-04 was 1 M $K_2HPO_4$/$KH_2PO_4$, pH 9.0;

(5) Washing the obtained DNA chip: three solutions were introduced for washing in a sequence of RI-05, RI-06 and RI-07, 3 times for each solution, wherein the volume introduced each time was 1 mL, the flow rate was 1 mL/min, and the temperature was maintained at 37° C. during the washing; RI-05 was phosphate buffer (pH 7.4), RI-06 was a mixture of 150 mM HEPES buffer and 150 mM NaCl solution, and RI-07 was double distilled water.

After washing with the three solutions and air-drying or oven-drying, the DNA chip of this example was obtained. The DNA chip prepared in this example was evaluated for the immobilized density by single-molecule fluorescence imaging, and specifically, the immobilized density of the DNA chip was represented by the number of Cy3 fluorescence dots per unit area by detecting Cy3 fluorescence on the DNA strand. In this example, the number of fluorescence dots in a region of 110×110 μm was counted to represent the immobilized density.

The results of the immobilized density assay are shown in FIG. 2. In FIG. 2, "Yes" on the abscissa represents the DNA chip treated with the weak passivation reaction solution containing CTAB and "No" represents the DNA chip treated with the weak passivation reaction solution containing no CTAB, and the ordinate represents the number of fluorescence dots per unit area of 110×110 μm.

FIG. 2 is a bar graph comparing the mean values of the DNA chips treated with the weak passivation reaction solution containing CTAB in 8 channels and those treated with the weak passivation reaction solution containing no CTAB in 8 channels among the 16 channels. The results in FIG. 2 show that in the weak passivation procedure, the DNA chip treated with the weak passivation reaction solution containing CTAB had an immobilized density of about 18000 Dot/FOV in a region of 110×110 m, while the DNA chip treated with the weak passivation reaction solution containing no CTAB had an immobilized density of only about 3000 Dot/FOV in a region of the same size; therefore, the weak passivation procedure added with CTAB can effectively increase the density of DNA per unit area, and the addition of CTAB can promote the sufficient binding of an amino group to an epoxy group.

Example II

The materials and procedures for preparing the DNA chip of this example were the same as those in Example I, except that the content of DNA in immobilization reaction solutions was 0.01 nM, 0.04 nM, 0.07 nM and 0.1 nM, respectively, during the immobilization, and the other conditions were the same as those in Example I, so as to verify the effect of different concentrations of DNA on the chip.

The procedures for preparing the DNA chip of this example are as follows:

(1) Immobilization: an immobilization reaction solution AT-01 containing 0.05 nM DNA (50 deoxythymidine monophosphates) was introduced into channels of the chip substrate for the immobilizing, wherein the 5' end of the contained DNA had both an amino modification $NH_2$ and a Cy3 fluorophore modification; AT-01 was 0.25 M $Na_2CO_3$/$NaHCO_3$ containing 0.6 mM CTAB, pH 9.78, the volume of the introduced solution was 1 mL, the flow rate was 1 mL/min, the reaction time was 30 min, and the reaction temperature was 37° C.;

in this example, the immobilization reaction solutions with DNA concentrations of 0.01 nM, 0.04 nM, 0.07 nM and 0.1 nM were introduced into different channels;

(2) Weak passivation: a weak passivation reaction solution was introduced for the "weak passivation", wherein the weak passivation reaction solution was 0.25 M $Na_2CO_3$/$NaHCO_3$ containing 10 mM CTAB, pH 9.58-10.53, specifically pH 9.78 in this example; the volume of the introduced solution was set to 1 mL, the flow rate was set to 1 mL/min, the reaction time was set to 3 h, and the reaction temperature was set to 37° C.;

compared with the Example III, in this example, the weak passivation reaction solution added with a small molecule modifier (specifically taurine) having a single negatively charged group was introduced into a part of the channels, and the weak passivation reaction solution without a small molecule modifier was introduced into the rest of the channels;

for all channels, the volume of the introduced solution was set to 1 mL, the flow rate was set to 1 mL/min, the reaction time was set to 3 h, and the reaction temperature was set to 37° C.;

(3) Washing away the weak passivation reaction solution: a passivation reaction solution RI-04 was introduced for washing for 3 times, wherein the volume introduced each time was 1 mL, the flow rate was 1 mL/min, and the temperature was maintained at 37° C. during the washing; RI-04 was 1 M $K_2HPO_4$/$KH_2PO_4$, pH 9.0;

(4) Passivation: a passivation reaction solution RI-04 was introduced for washing for 3-4 times, wherein the volume introduced each time was 500 L, the flow rate was 1 mL/min, the time interval between introductions was 1800 s, and the temperature was maintained at 37° C. during the passivation; RI-04 was 1 M $K_2HPO_4$/$KH_2PO_4$, pH 9.0;

(5) Washing the obtained DNA chip: three solutions were introduced for washing in a sequence of RI-05, RI-06 and RI-07, 3 times for each solution, wherein the volume introduced each time was 1 mL, the flow rate was 1 mL/min, and the temperature was maintained at 37° C. during the washing; RI-05 was phosphate buffer (pH 7.4), RI-06 was a mixture of 150 mM HEPES buffer and 150 mM NaCl solution, and RI-07 was double distilled water.

After washing with the three solutions and air-drying or oven-drying, the DNA chip of this example was obtained.

The DNA chip of this example was assayed by the same method as that in Example I, and the results are shown in FIG. 3. In FIG. 3, the abscissa represents different concentrations of DNA, and the ordinate represents the corresponding number of fluorescence dots per unit area of 110×110 m. The results in FIG. 3 show that the number of Cy3 fluorescence dots per unit area increased with the increase of the initial DNA concentration, i.e., the immobilized density of the DNA chip correspondingly increased, suggesting that the method for preparing a DNA chip in this example has a good dependence on the initial DNA concentration, and the amount of DNA immobilized on the DNA chip can be controlled by adjusting the initial DNA concentration.

Example III

In this example, a DNA chip was prepared by immobilizing a DNA, through an amino group of the DNA, on a glass substrate having epoxy silane on the surface thereof. In the preparation process, a weak passivation procedure was added between the immobilization and passivation procedures. In this example, the effect of small molecule modifiers on a DNA chip was shown.

In this example, the DNA was immobilized on the chip substrate by "in-channel" immobilization, specifically, the chip substrate was packaged, and then various reagents and detergents are introduced into the packaged chip channels by using a fluid device, such that chemical reactions such as immobilization and passivation were performed. As shown in FIG. 1, independent chip channels were formed in the packaged chip substrate, and each chip channel could independently perform the reactions. FIG. 1 shows a packaged chip substrate with 8 independent chip channels with the specification of 90 mm×1.8 mm×0.1 mm in length×width×height. The chip substrate can be packaged into 16 channels according to different packaging processes or fluid devices as well, and 16 kinds of DNAs with different modifications are independently prepared on one DNA chip.

The procedures for preparing the DNA chip of this example are as follows:

(1) Immobilization: an immobilization reaction solution AT-01 containing 0.05 nM DNA and 0.6 mM CTAB was introduced into channels of the chip substrate for the immobilization, wherein the 3' end of the contained DNA had both an amino modification $NH_2$ and a Cy3 fluorophore modification; AT-01 was 0.25 M $Na_2CO_3$/$NaHCO_3$ containing 0.6 mM CTAB, pH 9.78, the volume of the introduced solution was 1 mL, the flow speed was 1 mL/min, the reaction time was 30 min, and the reaction temperature was 37° C.;

(2) Weak passivation: a weak passivation reaction solution was introduced for the "weak passivation", wherein the weak passivation reaction solution was 0.25 M $Na_2CO_3$/$NaHCO_3$ containing 10 mM CTAB and 30 mM small molecule modifier, pH 9.58-10.53, specifically pH 9.78 in this example; for comparison, the weak passivation reaction solution added with a small molecule modifier (specifically taurine) having a single negatively charged group was introduced into a part of the channels, and the weak passivation reaction solution without a small molecule modifier was introduced into the rest of the channels; for all channels, the volume of the introduced solution was set to 1 mL, the flow rate was set to 1 mL/min, the reaction time was set to 3 h, and the reaction temperature was set to 37° C.;

(3) Washing away the weak passivation reaction solution: a passivation reaction solution RI-04 was introduced for washing for 3 times, wherein the volume introduced each time was 1 mL, the flow rate was 1 mL/min, and the temperature was maintained at 37° C. during the washing; RI-04 was 1 M $K_2HPO_4$/$KH_2PO_4$, pH 9.0;

(4) Passivation: a passivation reaction solution was introduced for the passivation, wherein the passivation reaction solution was 0.25 M $Na_2CO_3$/$NaHCO_3$ containing 30 mM small molecule modifier, pH 9.58-10.53, specifically pH 9.78 in this example; the passivation reaction solution was introduced for 3-4 times, the volume introduced each time was 500 L, the flow rate was 1 mL/min, the time interval between introductions was 1800 s, and the temperature was maintained at 37° C. during the passivation; the small molecule modifier in the passivation reaction solution corresponded to taurine used in the weak passivation, that is, the passivation reaction solution added with taurine was introduced into a corresponding channel involving taurine in the weak passivation procedure;

(5) Washing the passivated DNA chip: three solutions were introduced for washing in a sequence of RI-05, RI-06 and RI-07, 3 times for each solution, wherein the volume introduced each time was 1 mL, the flow rate was 1 mL/min, and the temperature was maintained at 37° C. during the washing; RI-05 was phosphate buffer (pH 7.4), RI-06 was a mixture of 150 mM HEPES buffer and 150 mM NaCl solution, and RI-07 was double distilled water.

After washing with the three solutions and air-drying or oven-drying, the DNA chip of this example was obtained. The nonspecific adsorption of the DNA chip prepared in this example was evaluated by single-molecule fluorescence imaging. The method for detecting the nonspecific adsorption is as follows: introducing a Cy5 fluorescence-labeled nucleotide on the surface of the prepared DNA chip, detecting Cy5 fluorescence adsorbed on the surface of the DNA chip, and representing the number of nonspecific adsorption dots of the DNA chip by the number of Cy5 fluorescence dots per unit area. In this example, the number of fluorescence dots in a region of 110×110 μm was counted to represent the nonspecific adsorption dots.

The results of the number of the nonspecific adsorption sites are shown in FIG. 5. In FIG. 5, "Taurine" on the abscissa indicates the DNA chip treated with taurine and "Null" indicates the DNA chip treated without a small molecule modifier, and the ordinate represents the number of fluorescence dots in the region of 110×110 Wm. The results in FIG. 5 show that the number of nonspecific adsorption dots of the DNA chip added with a small molecule modifier taurine having a single negatively charged group was about 1000 Dot/FOV, which was much lower than that of the DNA chip without a small molecule modifier. Therefore, the small molecule modifier having a single negatively charged group has a good nonspecific adsorption resistance effect.

Example IV

The materials and procedures for preparing the DNA chip of this example were the same as those in Example I, except that a small molecule modifier having multiple negatively charged groups and a small molecule modifier having a single negatively charged group were added separately in this example, and the effects of different small molecule modifiers on the DNA chip were compared. Specifically, in this example, the nonspecific adsorption resistance effects of a small molecule modifier taurine having a single negatively charged group and small molecule modifiers glutamic acid and phospho-serine having multiple negatively charged groups were compared.

The procedures for preparing the DNA chip of this example are as follows:

(1) Immobilization: an immobilization reaction solution AT-01 containing 0.05 nM DNA and 0.6 mM CTAB was introduced into channels of the chip substrate for the immobilization, wherein the 3' end of the contained DNA had both an amino modification $NH_2$ and a Cy3 fluorophore modification; AT-01 was 0.25 M $Na_2CO_3$/$NaHCO_3$ containing 0.6 mM CTAB, pH 9.78, the volume of the introduced solution was 1 mL, the flow rate was 1 mL/min, the reaction time was 30 min, and the reaction temperature was 37° C.;

(2) Weak passivation: a weak passivation reaction solution was introduced for the "weak passivation", wherein the weak passivation reaction solution was 0.25 M $Na_2CO_3$/$NaHCO_3$ containing 10 mM CTAB and 30 mM small molecule modifier, pH 9.58-10.53, specifically pH 9.78 in this example; for comparison, the weak passivation reaction solution added with a small molecule modifier (specifically taurine) having a single negatively charged group was introduced into a part of the channels, the weak passivation reaction solution added with a small molecule modifier (glutamic acid) having multiple negatively charged groups was introduced into another part of the channels, and the weak passivation reaction solution added with a small molecule modifier (phospho-serine) having multiple negatively charged groups was introduced into yet another part of the channels; for all channels, the volume of the introduced solution was set to 1 mL, the flow rate was set to 1 mL/min, the reaction time was set to 3 h, and the reaction temperature was set to 37° C.;

it should be noted that in the weak passivation procedure and the subsequent passivation procedure, the added small molecule modifiers may be the same or different; in general, the small molecule modifiers added in both procedures are the same;

(3) Washing away the weak passivation reaction solution: a passivation reaction solution RI-04 was introduced for washing for 3 times, wherein the volume introduced each time was 1 mL, the flow rate was 1 mL/min, and the temperature was maintained at 37° C. during the washing; RI-04 was 1 M $K_2HPO_4/KH_2PO_4$, pH 9.0;

(4) Passivation: a passivation reaction solution was introduced for the passivation, wherein the passivation reaction solution was 0.25 M $Na_2CO_3/NaHCO_3$ containing 30 mM small molecule modifier, pH 9.58-10.53, and specifically pH 9.78 in this example; the passivation reaction solution was introduced for 3-4 times, the volume introduced each time was 500 L, the flow rate was 1 mL/min, the time interval between introductions was 1800 s, and the temperature was maintained at 37° C. during the passivation; the small molecule modifier in the passivation time interval between introductions corresponded to taurine, glutamic acid or phospho-serine used in the weak passivation, that is, the passivation reaction solution added with taurine, glutamic or phospho-serine was introduced respectively into a corresponding channel involving taurine, glutamic or phospho-serine in the weak passivation procedure;

(5) Washing the passivated DNA chip: three solutions were introduced for washing in a sequence of RI-05, RI-06 and RI-07, 3 times for each solution, wherein the volume introduced each time was 1 mL, the flow rate was 1 mL/min, and the temperature was maintained at 37° C. during the washing; RI-05 was phosphate buffer (pH 7.4), RI-06 was a mixture of 150 mM HEPES buffer and 150 mM NaCl solution, and RI-07 was double distilled water.

After washing with the three solutions and air-drying or oven-drying, the DNA chip of this example was obtained.

The DNA chip of this example was assayed by the same method as that in Example III, and the results are shown in FIG. 6. In FIG. 6, the abscissa indicates different small molecule modifiers, and the ordinate indicates the number of nonspecific adsorption fluorescence dots per unit area of 110×110 m corresponding to different small molecule modifiers. The results in FIG. 6 show that the number of nonspecific adsorption dots of the DNA chip treated with a small molecule modifier taurine having a single negatively charged group was about 1000 Dot/FOV, that of the DNA treated with a small molecule modifier glutamic acid having multi-negatively charged groups was about 800 Dot/FOV, and that of the DNA chip treated with a small molecule modifier phospho-serine having multiple negatively charged groups was about 650 Dot/FOV; therefore, the numbers of nonspecific adsorption dots of taurine, glutamic acid and phospho-serine are in a descending order, suggesting that the small molecule modifier having multiple negatively charged groups is superior to the small molecule modifier having a single negatively charged group, and has better nonspecific adsorption resistance effect.

Example V

The materials and procedures for preparing the DNA chip of this example were the same as those in Example I, except that the effects of adding an accelerant or not to the DNA chip added with a small molecule modifier during the passivation were compared. The accelerant added in this example was benzyltriethylammonium chloride.

The procedures for preparing the DNA chip of this example are as follows:

(1) Immobilization: an immobilization reaction solution AT-01 containing 0.05 nM DNA and 0.6 mM CTAB was introduced into channels of the chip substrate for the immobilization, wherein the 3' end of the contained DNA had both an amino modification $NH_2$ and a Cy3 fluorophore modification; AT-01 was 0.25 M $Na_2CO_3/NaHCO_3$, pH 9.78, the volume of the introduced solution was 1 mL, the flow rate was 1 mL/min, the reaction time was 30 min, and the reaction temperature was 37° C.;

(2) Weak passivation: a weak passivation reaction solution was introduced for the "weak passivation", wherein the weak passivation reaction solution was 0.25 M $Na_2CO_3/NaHCO_3$ containing 10 mM CTAB and 30 mM small molecule modifier, pH 9.58-10.53, specifically pH 9.78 in this example; the small molecule modifier is taurine; for all channels, the volume of the introduced solution was set to 1 mL, the flow rate was set to 1 mL/min, the reaction time was set to 3 h, and the reaction temperature was set to 37° C.;

(3) Washing away the weak passivation reaction solution: a passivation reaction solution RI-04 was introduced for washing for 3 times, wherein the volume introduced each time was 1 mL, the flow rate was 1 mL/min, and the temperature was maintained at 37° C. during the washing; RI-04 was 1 M $K_2HPO_4/KH_2PO_4$, pH 9.0;

(4) Passivation: a passivation reaction solution was introduced for the passivation, wherein the passivation reaction solution was 0.25 M $Na_2CO_3/NaHCO_3$ containing 30 mM small molecule modifier taurine, pH 9.58-10.53, specifically pH 9.78 in this example; the passivation reaction solution was introduced for 3-4 times, the volume introduced each time was 500 L, the flow rate was 1 mL/min, the time interval between introductions was 1800 s, and the temperature was maintained at 37° C. during the passivation; for comparison, channels to which the passivation reaction solutions with or without accelerant benzyltriethylammonium chloride were introduced were provided, and the concentration of benzyltriethylammonium chloride in passivation reaction solution containing the same was 30 mM;

(5) Washing the passivated DNA chip: three solutions were introduced for washing in a sequence of RI-05, RI-06 and RI-07, 3 times for each solution, wherein the volume introduced each time was 1 mL, the flow rate was 1 mL/min, and the temperature was maintained at 37° C. during the washing; RI-05 was phosphate buffer (pH 7.4), RI-06 was a mixture of 150 mM HEPES buffer and 150 mM NaCl solution, and RI-07 was double distilled water.

After washing with the three solutions and air-drying or oven-drying, the DNA chip of this example was obtained.

Figure 7:
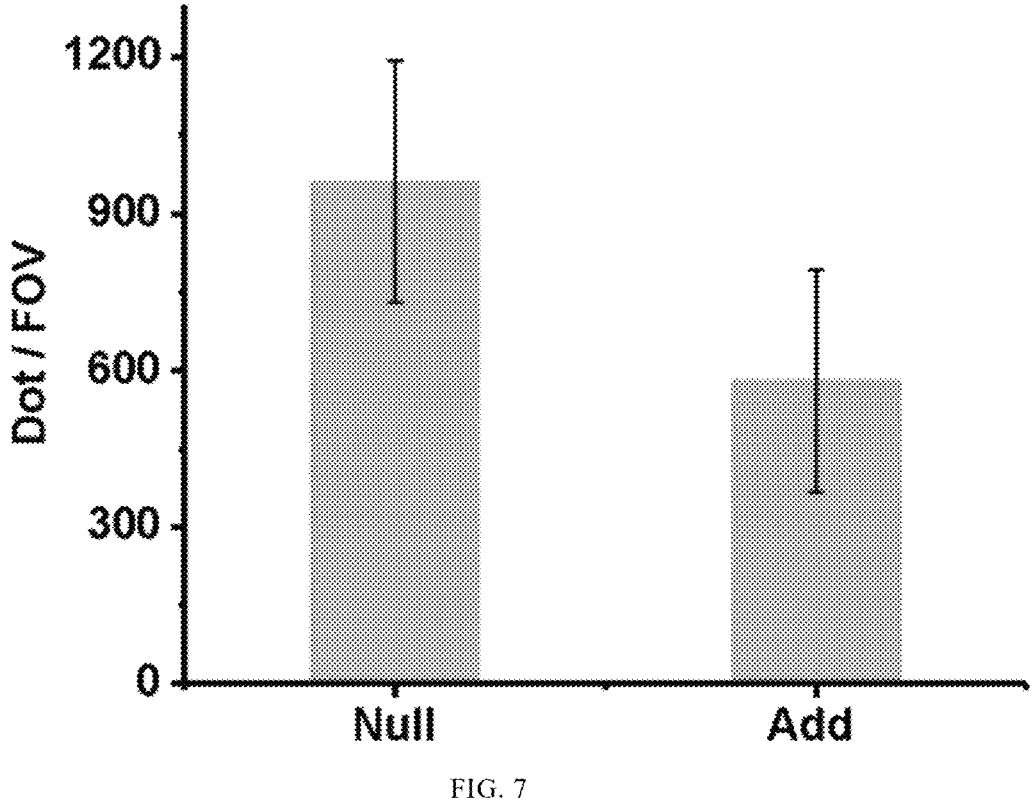
FIG. 7 is a graph showing the results of the nonspecific adsorption experiment on the DNA chip added with or without an accelerant in Example V.

The DNA chip of this example was assayed by the same method as that in Example II, and the results are shown in FIG. 7. In FIG. 7, Null on the abscissa indicates DNA chips without accelerant, Add indicates DNA chips with accelerant, and the ordinate indicates the number of nonspecific adsorption fluorescence dots in corresponding 110×110 μm unit area. The results in FIG. 7 show that the number of nonspecific adsorption fluorescence dots of the corresponding DNA chip after the accelerant was added was about 600 Dot/FOV, while the number of nonspecific adsorption fluorescence dots of the DNA chip without the accelerant was about 1000 Dot/FOV, indicating that the accelerant can further promote the binding of the small molecule modifier taurine to the substrate, thereby further reducing the nonspecific adsorption on the DNA chip.

Example VI

In this example, the protein co-modified DNA chip was prepared by immobilizing a DNA, through an amino group of the DNA, on a glass substrate having epoxy silane on the surface thereof, and using BSA as co-modification protein. In this example, the effects of the co-modification with and without the addition of BSA on the DNA chip were compared.

In this example, the DNA was immobilized on the chip substrate by "in-channel" immobilization, specifically, the chip substrate was packaged, and then various reagents and detergents are introduced into the packaged chip channels by using a fluid device, such that chemical reactions such as immobilization and passivation were performed. As shown in FIG. 1, independent chip channels were formed in the packaged chip substrate, and each chip channel could independently perform the reactions. FIG. 1 shows a packaged chip substrate with 8 independent chip channels with the specification of 90 mm×1.8 mm×0.1 mm in length×width×height. The chip substrate can be packaged into 16 channels according to different packaging processes or fluid devices as well, and 16 kinds of DNAs with different modifications can be independently prepared on one DNA chip.

The procedures for preparing the DNA chip of this example are as follows:

(1) Immobilization: an immobilization reaction solution AT-01 containing 0.2 nM DNA and 30 μM BSA was introduced into channels of the chip substrate for the immobilization, wherein the 3' end of the contained DNA had both an amino modification $NH_2$ and a Cy3 fluorophore modification; AT-01 was 0.25 M $Na_2CO_3$/$NaHCO_3$ containing 0.6 mM CTAB, pH 9.78, the volume of the introduced solution was 1 mL, the flow rate was 1 mL/min, the reaction time was 30 min, and the reaction temperature was 37° C.;

as a control, a channel to which the immobilization reaction solution without BSA was introduced was provided in this example;

the DNA and BSA are in a competitive relationship for adsorption, and the adsorption performance of the DNA on the surface is far better than that of the BSA, such that even if BSA was added with a 15000-fold concentration, the influence on DNA modification was insignificant; in the preparation method of this example, BSA was added during the immobilization and the weak passivation, giving a better protein co-modification effect; obviously, BSA can be added only in the immobilization procedure in a condition of lower requirements;

(2) Weak passivation: a weak passivation reaction solution was introduced for the "weak passivation", wherein the weak passivation reaction solution was 0.25 M $Na_2CO_3$/$NaHCO_3$ containing 10 mM CTAB, 30 mM taurine and 30 M BSA, pH 9.58-10.53, specifically pH 9.78 in this example; the volume of the introduced solution was set to 1 mL, the flow rate was set to 1 mL/min, the reaction time was set to 3 h, and the reaction temperature was set to 37° C.; as a control, a channel to which the reaction solution without BSA was introduced during immobilization did not involve the addition of BSA in the reaction solution introduced thereto during weak passivation, with the rest components, the amount and the channel parameter setting being the same;

(3) Washing away the weak passivation reaction solution: a passivation reaction solution RI-04 was introduced for washing for 3 times, wherein the volume introduced each time was 1 mL, the flow rate was 1 mL/min, and the temperature was maintained at 37° C. during the washing; RI-04 was 1 M $K_2HPO_4$/$KH_2PO_4$, pH 9.0;

(4) Passivation: a passivation reaction solution RI-04 was introduced for washing for 3-4 times, wherein the volume introduced each time was 500 L, the flow rate was 1 mL/min, the time interval between introductions was 1800 s, and the temperature was maintained at 37° C. during the passivation; RI-04 was 1 M $K_2HPO_4$/$KH_2PO_4$, pH 9.0;

(5) Washing the passivated DNA chip: three solutions were introduced for washing in a sequence of RI-05, RI-06 and RI-07, 3 times for each solution, wherein the volume introduced each time was 1 mL, the flow rate was 1 mL/min, and the temperature was maintained at 37° C. during the washing; RI-05 was phosphate buffer (pH 7.4), RI-06 was a mixture of 150 mM HEPES buffer and 150 mM NaCl solution, and RI-07 was double distilled water.

After washing with the three solutions and air-drying or oven-drying, the DNA chip of this example was obtained.

The non-specific protein adsorption of the DNA chip prepared in the embodiment was evaluated by a single-molecule fluorescence imaging technique; specifically, Klenow Fragment with a fluorescent label was introduced to the surface of the prepared DNA chip, the number of the fluorescent labels of the Klenow Fragment adsorbed on the surface of the DNA chip was detected, and the non-specific protein adsorption on the DNA chip was represented by the number of the fluorescent labels of the Klenow Fragment in unit area. In this example, the number of fluorescence dots in a region of 110×110 μm was counted.

Figure 8:
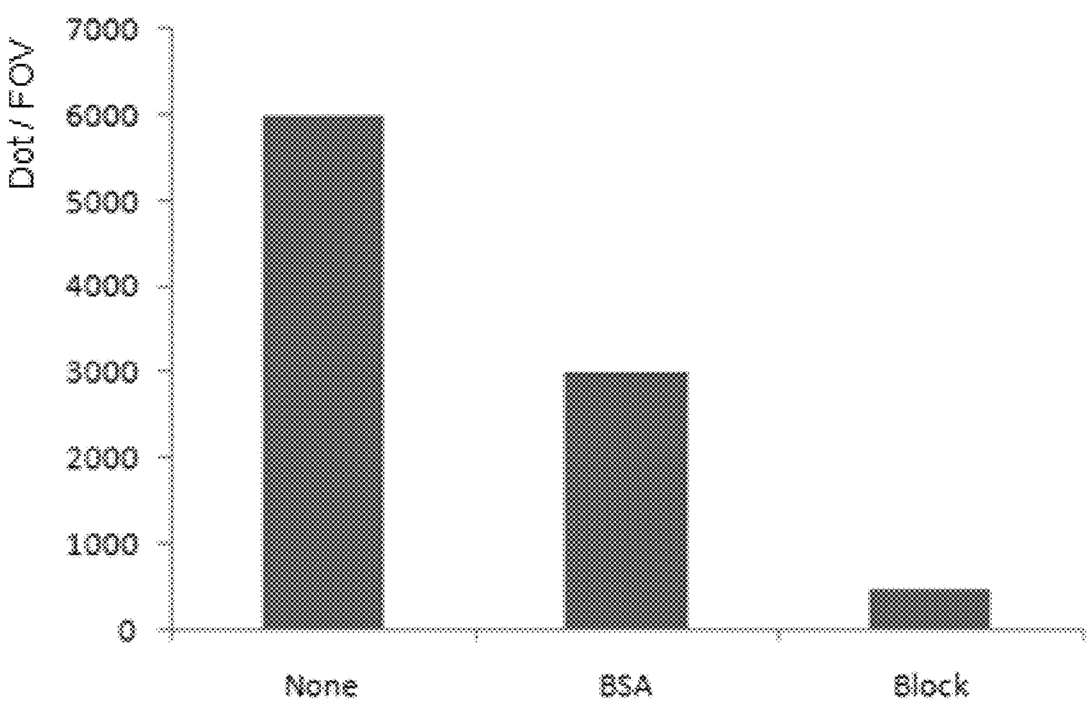
FIG. 8 is a graph showing the comparison of the adsorption results of the protein-modified chips to proteins in a test system in Examples VI to VII of the present application, where None is for a DNA chip without BSA; BSA is for a protein co-modified DNA chip prepared by adding BSA for co-modification; Block is for a DNA chip prepared by sulfydryl blocking with BSA co-modification.

The test results of the DNA chip and the control test of this example are shown in FIG. 8. In FIG. 8, None on the abscissa indicates a DNA chip involving the addition of BSA, BSA indicates a protein co-modified DNA chip prepared by co-modification with BSA, and the ordinate indicates the number of corresponding fluorescence dots. The results in FIG. 8 show that the number of nonspecific adsorption dots on the DNA chips prepared after the co-modification with BSA was about 3000 Dot/FOV, while that of the DNA chips prepared without the co-modification with BSA was more than 6000 Dot/FOV, suggesting that the BSA co-modification can greatly reduce the nonspecific adsorption of protein on the DNA chip, and has good protein adsorption resistance.

Example VII

The materials and procedures for preparing the DNA chip of this example are the same as those in Example VI, except that after the passivation, sulfydryl blocking was added, and the sulfydryl blocking reagent was used to block the sulfydryl groups on the protein, so as to reduce the nonspecific adsorption of sulfydryl small molecules on the protein-co-modified DNA chip.

The procedures for preparing the DNA chip of this example are as follows:

(1) Immobilization: an immobilization reaction solution AT-01 containing 0.2 nM DNA and 30 M BSA was introduced into channels of the chip substrate for the immobilization, wherein the 3' end of the contained DNA had both an amino modification $NH_2$ and a Cy3 fluorophore modification; AT-01 was 0.25 M $Na_2CO_3$/$NaHCO_3$ containing 0.6 mM CTAB, pH 9.78, the volume of the introduced solution was 1 mL, the flow rate was 1 mL/min, the reaction time was 30 min, and the reaction temperature was 37° C.;

(2) Weak passivation: a weak passivation reaction solution was introduced for the "weak passivation", wherein the weak passivation reaction solution was 0.25 M $Na_2$ $CO_3$/$NaHCO_3$ containing 10 mM CTAB, 30 mM taurine and 30 M BSA, pH 9.58-10.53, specifically pH 9.78 in this example; the volume of the introduced solution was set to 1 mL, the flow rate was set to 1 mL/min, the reaction time was set to 3 h, and the reaction temperature was set to 37° C.; (3) Washing away the weak passivation reaction solution: a passivation reaction solution RI-04 was introduced for washing for 3 times, wherein the volume introduced each time was 1 mL, the flow rate was 1 mL/min, and the temperature was maintained at 37° C. during the washing; RI-04 was 1 M $K_2HPO_4$/$KH_2PO_4$, pH 9.0;

(4) Passivation: a passivation reaction solution RI-04 was introduced for washing for 3-4 times, wherein the volume introduced each time was 500 L, the flow rate was 1 mL/min, the time interval between introductions was 1800 s, and the temperature was maintained at 37° C. during the passivation; RI-04 was 1 M $K_2HPO_4$/$KH_2PO_4$, pH 9.0;

(5) Sulfydryl blocking: a) a reaction solution containing reductant TCEP was introduced, which was a mixture of 150 mM Tris, pH 8.0, 100 mM NaCl and 30 mM TCEP; the purpose of this procedure was to reduce the disulfide bond in the system, forming reductive sulfydryl groups and facilitating the subsequent blocking; the volume of the introduced solution was 1 mL, the flow rate was 1 mL/min, the reaction time was 10-30 min, and the reaction temperature was 37° C.; b) a sulfydryl blocking reagent was introduced, which may be iodoacetamide or iodoacetic acid, and in the example, the iodoacetamide was used; the reaction solution was a mixture of 150 mM HEPES, pH 8.5, 100 mM NaCl and 30 mM iodoacetamide, the volume of the introduced solution was 1 mL, the flow rate was 1 mL/min, the reaction time was 10-30 min, specifically 30 min in this example, and the reaction temperature was 37° C.;

(6) Washing the blocked DNA chip: three solutions were introduced for washing in a sequence of RI-05, RI-06 and RI-07, 3 times for each solution, wherein the volume introduced each time was 1 mL, the flow rate was 1 mL/min, and the temperature was maintained at 37° C. during the washing; RI-05 was phosphate buffer (pH 7.4), RI-06 was a mixture of 150 mM HEPES buffer and 150 mM NaCl solution, and RI-07 was double distilled water.

After washing with the three solutions and air-drying or oven-drying, the DNA chip of this example was obtained.

The adsorption of nucleotide molecules containing disulfide bonds on the DNA chip prepared in this example was evaluated by a single-molecule fluorescence imaging technique; specifically, nucleotide molecules containing disulfide bonds with a fluorescent Cy3 label was introduced to the surface of the prepared DNA chip, the quantity of Cy3 fluorescence adsorbed on the surface of the DNA chip was detected, and the adsorption of nucleotide molecules containing disulfide bonds on the DNA chip was represented by the quantity of Cy3 fluorescence in unit area. In this example, the number of fluorescence dots in a region of 110×110 μm was counted. Meanwhile, the adsorption of small molecules with disulfide bonds on the DNA chip prepared by BSA co-modification in Example VI was tested for comparison, in which the DNA chips prepared by BSA co-modification were not subjected to sulfydryl blocking. The disulfide bond-containing nucleotide molecules used in this example can be found in EP2607369B1, and the specific molecular structure is shown in FIG. 8 of this patent application.

The results are shown in FIG. 8, in which "BSA" on the abscissa indicates DNA chips of BSA co-modification without sulfydryl blocking, i.e., the BSA co-modification DNA chip of Example V, and "Block" indicates the DNA chip of BSA co-modification with sulfydryl blocking, i.e., the DNA chip of this example. The results in FIG. 8 show that the number of non-specific adsorption dots on the DNA chip without sulfydryl blocking was more than 3000 Dot/FOV, while that on the DNA chip with sulfydryl blocking was about 500 Dot/FOV, suggesting that the non-specific adsorption of the small molecule substance containing sulfydryl groups on the DNA chip can be greatly reduced by sulfydryl blocking.

In the specification, terms such as "one embodiment", "some embodiments", "one or some specific embodiments", "one or some examples", "exemplary" or the like, means that a particular feature, structure, material or characteristic described in reference to the embodiment or example is included in at least one embodiment or example of the present disclosure. In the specification, the schematic description of the aforementioned terms do not necessarily refer to the same embodiment or example. Moreover, the specific features, materials, structures and other characteristics described may be combined in any one or more embodiments or examples in an appropriate manner. Moreover, various embodiments or examples and features of various embodiments or examples described in this specification can be combined by one skilled in the art to the extent that they do not contradict each other.

Although embodiments of the present invention are illustrated and described above, it will be appreciated that the above embodiments are exemplary and not to be construed as limiting the present invention, and that changes, modifications, substitutions and alterations can be made to the above embodiments by those of ordinary skill in the art within the scope of the present invention.

What is claimed is:

1. A substrate comprising a surface, the surface coated with an anti-nonspecific adsorption layer, the anti-nonspecific adsorption layer comprising a small molecule modifier selected at least one from the compounds having the structural formula I, (I)

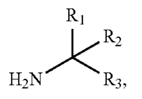

wherein $R_1$, $R_2$ and $R_3$ are each independently selected from a hydrophilic group or a hydrogen atom;

wherein the surface is a chemically modified surface comprising an active group selected from at least one of epoxy group, formyl, carboxyl, N-hydroxysuccinimide and diaminobenzanilide group; and wherein the surface is immobilized with oligonucleotides and protein molecules, and the oligonucleotides and the protein molecules are immobilized on the substrate surface through a covalent bond between an amino group of DNA or protein and an active group on the substrate surface, wherein sulfydryl groups on the protein molecules are blocked by epoxy propanol.

2. The substrate of claim 1, wherein the hydrophilic group is a negatively charged group.

3. The substrate of claim 1, wherein the hydrophilic group comprises a phosphate group, a phosphate ester group, a sulfonate group, a carboxylate group, a hydroxyl group, or an amide group.

4. The substrate of claim 2, wherein the small molecule modifier is selected at least one from taurine, aminopropanesulfonic acid, serine, glutamic acid and phospho-serine.

5. The substrate of claim 2, wherein the small molecule modifier is covalently attached to the surface.

6. A biochip comprising the substrate of claim 1.

* * * * *